United States Patent [19]

Loev

[11] Patent Number: 5,166,149
[45] Date of Patent: Nov. 24, 1992

[54] METHOTREXATE COMPOSITIONS AND METHODS OF TREATMENT USING SAME

[75] Inventor: Bernard Loev, Scarsdale, N.Y.

[73] Assignee: Chemex Pharmaceuticals, Inc., Fort Lee, N.J.

[21] Appl. No.: 713,558

[22] Filed: Jun. 10, 1991

Related U.S. Application Data

[63] Continuation of Ser. No. 404,424, Sep. 8, 1989, abandoned.

[51] Int. Cl.$^5$ .......................................... A61K 31/555
[52] U.S. Cl. .................................... 514/186
[58] Field of Search ................ 424/641; 514/521, 186

[56] References Cited

U.S. PATENT DOCUMENTS 4,136,101  1/1979  Kazan .
4,375,987  2/1983  Singh et al. .

OTHER PUBLICATIONS

Weinstein et al., Arch. Dermatol. 125:227 (1989).
Ball et al., J. Invest. Dermatol. 79:7 (1982).
Newburger et al., J. Invest. Dermatol. 70:183 (1978).
McCullough et al, J. Invest. Dermatol. 66:103 (1976).
Pratt et al, Cancer Cemother. Rep. Part 3 6:13 (1975).
Stewart et al., Arch. Dermatol. 106:357 (1972).
Weinstein, "Advanced in Biology of the Skin" vol. XII, *Pharmacology and the Skin* ed. Montagna et al. p. 287 et seq. (1969).
Comaish et al., Arch. Dermatol. 100:99 (1969).
Nurse, Arch. Dermatol. 87:258 (1963).
Van Scott et al. J. Invest. Dermatol. 33:357 (1959).

*Primary Examiner*—Frederick E. Waddell
*Assistant Examiner*—Zohreh A. Fay
*Attorney, Agent, or Firm*—Kenyon & Kenyon

[57] ABSTRACT

Compositions containing metal salts of methotrexate and methotrexate derivatives or analogs are disclosed. Such compositions comprise a metal salt, preferably a zinc salt, of methotrexate or a methotrexate derivative or analog and a carrier suitable for delivering the metal salt in the desired pharmacological form. Methods of treatment are also disclosed in which such compositions are topically applied or orally or parenterally administered to a patient. The metal salt is present in the treating composition in an amount sufficient to produce the desired therapeutic effect upon application or administration.

11 Claims, No Drawings

METHOTREXATE COMPOSITIONS AND METHODS OF TREATMENT USING SAME

This is a continuation of copending application Ser. No. 07/404,424 filed on Sep. 8, 1989 now abandoned.

FIELD OF THE INVENTION

The present invention relates to pharmaceutical compositions useful for administration of therapeutic doses of methotrexate to a patient. More particularly, the present invention relates to the use of metal salts of methotrexate and its analogs and derivatives in compositions which are administered topically or systemically. The zinc salts of methotrexate are most preferred.

BACKGROUND OF THE INVENTION

Methotrexate (also known as MTX; N-(4-[(2,4-diamino-6-pteridinyl)methyl]methylamino]benzoyl) glutamic acid; 4-amino-N-10-methylpteroyl glutamic acid; 4-amino-10-methyl folic acid; methylaminopterin; and amethopterin) is a folic acid analog and antagonist. Methotrexate has been therapeutically employed in numerous chemotherapeutic applications, including the treatment of psoriasis, leukemia, cancers and other disorders resulting from cell proliferation. Methotrexate has also been used as an immunosuppressant and for treating dermatomyositis and rheumatoid arthritis.

Methotrexate has been shown to demonstrate therapeutic effects when administered orally or parenterally. For example, massive doses of methotrexate followed by leucovorin rescue are employed in the clinical treatment of certain neoplasms [Pratt et al., Cancer Chemother. Rep. Part 3, 6:13 (1975)]. However, when methotrexate is administered in amounts sufficient to produce the desired therapeutic effect, toxicity and other adverse effects have frequently been observed. In this regard, methotrexate has been reported to cause fetal death and/or congenital anomalies when administered to women of childbearing potential. Hepatotoxicity has also been observed as a result of the administration of methotrexate, with concomitant elevation in liver enzymes, fatty change, portal inflammation, fibrosis and cirrhosis. Methotrexate has also been associated with induced lung disease, bone marrow depression (with associated anemia, leukopenia and/or thrombocytopenia), diarrhea, ulcerative stomatitis and hemorrhagic enteritis.

Orally administered methotrexate has been found to be particularly effective for the treatment of psoriasis, a skin disease characterized by hyperproliferation. However, because of significant systemic toxicity, the use of methotrexate is limited primarily to the most serious and extensive cases of psoriasis and therefore is of limited utility when administered by that route. Because of the side effects associated with known means of administration of methotrexate, alternative means for administration have been examined. Topical application of methotrexate has been pursued, but has proven unsatisfactory for one reason or another. [see, e.g., Stewart et al., Arch. Dermatol. 106:357 (1972); Weinstein, Advances in Biology of the Skin, Vol. XII, Pharmacology and the Skin, ed. Montagna et al., pp. 287 (Appleton-Century-Crofts, New York 1969); Comaish et al., Arch. Dermatol. 100:99 (1969); Nurse, Arch. Dermatol. 87:258 (1963); Van Scott et al., J. Invest. Dermatol. 33:357 (1959)].

One such reason is that methotrexate is a water-soluble drug and as such does not readily penetrate the stratum corneum, the outermost layer of the skin. It also cannot easily penetrate the lower skin layers to reach the epidermal or other cells upon which it is to act. The hydrophobic stratum corneum layer of the skin acts like a sieve which, probably due to the water solubility of methotrexate, is impenetrable to more than very small amounts of compound. It is likely that this lack of penetration into the skin is one of the primary reasons for lack of efficacy of the drug when applied topically. This is supported by the finding that direct intralesional administration of methotrexate into psoriatic plaques, which avoids penetration of the skin, is associated with a decrease in mitotic activity and hence a decreased proliferation in the treated area.

Although previous studies have shown that, when topically applied, some methotrexate trickles through the stratum corneum, the amount passing through is far less than the amount originally applied to the skin. As a result, for topical application of methotrexate to be effective at all, methotrexate must be applied in highly excessive amounts which leads to toxic reactions and other side effects.

Many attempts have been made to increase the percutaneous penetration and absorption of methotrexate. Most methods involve attempts to alter the solubility characteristics of methotrexate or the vehicle by which it is topically applied. For example, McCullough et al. (J. Invest. Dermatol. 66:103 107 (1976)) applied methotrexate in combination with dimethylsulfoxide (80%) or dimethylacetamide (25%) as a vehicle, with no effect on penetration. Although a 0.1% retinoic acid vehicle did not increase penetration, a saturated solution of retinoic acid in aqueous ethanol produced a marked increase. Decyl methyl sulfoxide (2.5%) produced a 143-fold increase in penetration, which approaches levels sufficient to produce the desired therapeutic effect in lower skin layers. Lipid soluble methotrexate derivatives (such as the dimethyl ester of dichloromethotrexate) were also tested and exhibited small increases in penetration. Ball et al. (J. Invest. Dermatol. 79:710 (1982)) also observed an increase in penetration using "Vehicle N" (alcohol 47.5%, water, laureth 4, isopropyl alcohol 4%, propyleneglycol) from Neutrogena Corporation.

Weinstein et al. [Arch. Dermatol. 25:227 (1989)] reported that a topical formulation of methotrexate in 1-dodecylazacycloheptan-2-one produced improvement in psoriatic patients. However, there were no statistical differences in drug treated versus vehicle treated sites one week after therapy was discontinued. Enhancement of methotrexate penetration into the affected skin in patients with psoriasis resulted in emprovement in the psoriatic plaques with no evidence of systemic side effects.

However, these methods have generally been shown to be disadvantageous in that the solvents used to enhance penetration may not be suitable for human use and to do so may present undesirable effects, including skin dehydration, irritation of sensitive skin, photosensitivity and changes in the lipid protein structure of the membranes.

Thus, the development of a pharmaceutical composition containing methotrexate which could be used locally on psoriatic plaques and would have a minimal systemic absorption would be expected to drastically reduce the toxicity of methotrexate and increase its utility for treatment of psoriasis and other disorders.

The ability to safely and efficaciously deliver methotrexate into the skin for the treatment of psoriasis and other hyperproliferative disorders is a requisite to widespread therapeutic use. To date, conventionally used formulations do not satisfactorily meet these requirements, thus impeding the clinical utility of methotrexate.

SUMMARY OF THE INVENTION

Thus, it is an object of the present invention to provide for pharmaceutical compositions for the treatment of psoriasis and other hyperproliferative disorders.

It is yet another object of the present invention to provide safe and efficacious pharmaceutical compositions for the treatment of psoriasis and other hyperproliferative disorders which can be administered parenterally or orally.

It is yet another object of the present invention to provide pharmaceutical compositions for the treatment of psoriasis and other hyperproliferative disorders which increase absorption and penetration of methotrexate thereby permitting the use of less methotrexate in the treatment of a patient.

These and other objects are achieved by pharmaceutical compositions containing metal salts of methotrexate, its analogs and derivatives and compositions containing such metal salts for the treatment of psoriasis and other hyperproliferative diseases of the skin. Although the pharmaceutical compositions according to the invention may be administered both parenterally and topically, topical application of the compositions directly to the situs of the hyperproliferative disorder is the most preferred route of administration.

DETAILED DESCRIPTION OF THE INVENTION

Administration of methotrexate in the form of a metal salt in accordance with the invention increases absorption and penetration of methotrexate. As compared to prior therapeutic preparations, lower concentrations of methotrexate may be employed in such compositions, thereby minimizing or eliminating the toxic effects usually associated with methotrexate therapy. The pharmaceutical compositions according to the invention are most effective when applied topically at the site of the hyperproliferative disorder.

The compositions according to the invention comprise a metal salt of methotrexate or a methotrexate derivative or analog and a carrier suitable for delivering the metal salt in the desired pharmacological form. Any suitable carrier (of which many will be known to skilled artisans) which will incorporate the metal salt at the desired concentration and in the desired form can be employed.

The metal salt may include any metal which forms salts with methotrexate including without limitation zinc, copper, cadmium and manganese. The zinc salts are preferred.

Carrier materials include without limitation water, buffers, excipients, binders, fillers, glidants, lubricants, emollients, humectants and surfactants. Compositions comprising a zinc salt of certain formulae without specifically requiring a carrier are also disclosed.

Alternate carriers (excipients) for topical dosage forms include without limitation the following: emollients, such as isopropyl myristate, caprylic/capric triglyceride, PEG-4, PEG-5, PEG-8, PEG-75 lanolin oil, PEG-2 laurate, isopropyl isostearate, isopropyl linoleate, isononyl isononanoate, diethyl sebacate, petrolatum, coconut oil, corn oil, olive oil, palm kernel oil, safflower oil, sunflower oil, glyceryl caprylate, diisopropyl dimerate; surfactants, such as polysorbate 40, polysorbate 80, polysorbate 20, ceteth-2, ceteth-20, steareth-2, steareth-21, PPG-15 stearyl ether, sorbitan palmitate, sorbitan stearate, sorbitan oleate, sorbitan tristearate, sorbitan trioleate; waxes, such as white wax, cetyl esters wax, spermaceti, cetearyl alcohol, paraffin, microcrystalline wax, PEG-150, PEG-350, carnauba wax, glyceryl tribehenate; and humectants, such as sodium lactate, lactic acid, pyrrolidone carboxylic acid, sodium PCA, collagen amino acids, and keratin amino acids.

Other additives can also be added to the liquid compositions for oral and topical use. Such additives include suspending agents such as acacia, carbomer 934, carboxymethylcellulose sodium, carragenin, gelatin, magnesium aluminum silicate, hydroxypropylcellulose, hydroxyethylcellulose and xanthan gum.

Methods of treatment are also disclosed in which such compositions are orally or parenterally administered or topically applied to a patient. The compositions can be orally administered as a solution, tablet, capsule or other acceptable oral form. Solutions, suspensions and other acceptable forms can be used for parenteral administration. Embodiments for topical application can employ compositions as solutions, lotions, creams, gels or other commonly used topical forms.

The metal salt is present in the treating composition in an amount sufficient to produce the desired therapeutic effect upon application or administration. When applied topically to an isolated skin site in need of treatment, there is a wide range of amounts of the components which may be utilized in the invention. For example, for topical use the formulation preferably contains from about 0.1% to about 10% methotrexate. For systemic administration, it is contemplated that the amount of methotrexate utilized in the composition to treat a patient be less than the known toxic value for methotrexate. Thus, for oral use, the formulation preferably contains between about 0.001 and 50 ug methotrexate. For parenteral use, concentrations between about 0.1 to 50 ug/ml are preferred.

The concentration ranges set forth herein are provided by way of description and not by way of limitation since it is recognized that the concentration may be adjusted over a wide range depending on a number of factors. Generally, the efficacious amount and concentration of the inhibitors are those which result in the composition exhibiting the property or properties required in the treatment for which the composition is being used, e.g., psoriasis or actinic keratosis. The preferred amounts depend upon the particular condition being treated, the severity of the condition, the method of delivery to the treatment site, e.g., topical or systemic, the rate of delivery of the active ingredients to the treatment site, the number of applications of the formulation which can be used, the other inhibitor used, the carrier material, etc. Preferred amounts for any specific application may be determined by normal pharmacological screening methods used in the art.

Processes for producing such compositions are discussed further below. Other means for combining metal salts with suitable carriers are known to skilled artisans.

In certain embodiments the zinc salt of methotrexate according to the invention is of the general formula (I), (II), (III) or (IV):

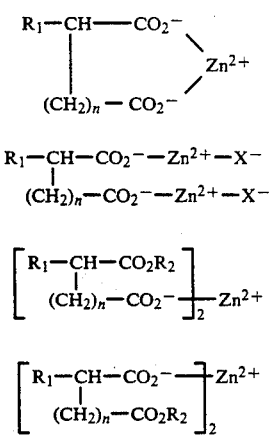

wherein n is 0 or an integer from 1 to 4, $X^-$ is an anion (preferably chloride, sulfate, phosphate, nitrate or the anionic form of an organic acid), wherein R2 is hydrogen or an aliphatic, aromatic or arylalkyl group, and R1 is of general formula (V):

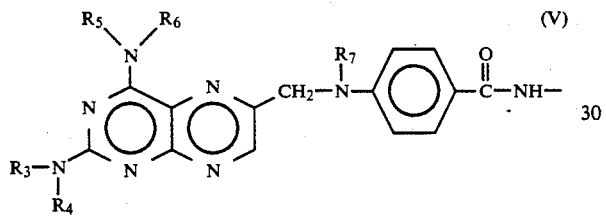

wherein R3, R4, R5, R6 and R7 are hydrogen or an alkyl group of 1 to 5 carbons.

In the preceding formulae (I)–(V), dotted lines indicate ionic bonds between the metal moiety and the connected functional group. For example, in formula (I), a single zinc ion is associated with both carboxyl groups of one methotrexate molecule. In formula (II), two different zinc ions are associated with the two different carboxyl groups. In formulae (III) and (IV), a single zinc ion is associated with carboxyl groups on two different methotrexate molecules.

Preferably, the salt is of general formula (III) or (IV) wherein R2, R3, R4, R5 and R6 are hydrogen, and R7 is methyl and n is 2.

Zinc salts of methotrexate can be produced by mixing together an aqueous solution of a water soluble zinc salt with an aqueous solution of a water soluble salt of methotrexate or with a solution of methotrexate in a water miscible solvent or in a mixture of a water miscible solvent and water. If a precipitate does not immediately form, the pH is adjusted to between 6 and 7 and the precipitated zinc methotrexate is filtered and washed with water or a water miscible solvent such as alcohol or acetone., and the precipitate is dried.

Another zinc salt of methotrexate of general formula (I) can be produced according to the method disclosed in U.S. Pat. No. 4,374,987.

The compositions and methods of the present invention should be useful for most indications for methotrexate therapy, including without limitation those previously discussed herein, and also as antibacterial, antiviral and antifungal agents.

The following examples are intended as exemplary and are not intended to limit the scope of the present invention which is defined by the appended claims.

EXAMPLE 1—PREPARATION OF ZINC SALT

A zinc salt of methotrexate was prepared as follows. Methotrexate (3.0 g, 0.0066 moles) was dissolved in 600 ml methanol at room temperature with rapid stirring. A solution of zinc acetate (0.6 g, 0.0033 moles) in 2 ml methanol was added dropwise to the methotrexate solution. Immediate precipitation (flocculent) was observed. The mixture was stirred for one hour at room temperature. The mixture was then concentrated in a rotating evaporator (roto-vap) at 40° C. The residue obtained (3.2 g) was dried under high vacuum. $(C_{20}H_{22}N_8O_5)_2Zn$, MW 974.29; percent zinc: 6.46 (found), 6.71 (theoretical).

EXAMPLE 2—PREPARATION OF ORAL DOSAGE FORM

| Tablet Formula | |
|---|---|
| Ingredient | Percent by Weight |
| Zinc methotrexate | 0.001–50.0 |
| Starch, pregelatinized | 10.000–5.0 |
| Microcrystalline cellulose | 10.000–5.0 |
| Lactose | 74.899–38.5 |
| Magnesium stearate | 0.100–0.5 |
| Guar gum | 5.000–1.0 |

The pregelatinized starch, microcrystalline cellulose, lactose, magnesium stearate and guar gum are added to a suitable blender (such as a V-blender) and blended for 15–45 minutes or until the contents have been blended uniformly. Zinc methotrexate is added to the above mix and blended to uniformity. This mix is then tabletted in a tableting machine in suitable size die cavities under predetermined pressure to obtain suitable size tablets. Alternate excipients for making these and other oral dosage forms include without limitation tribasic calcium phosphate, carboxymethylcellulose sodium, hydroxypropyl methylcellulose, methylcellulose, polyethylene glycol, sodium starch glycolate, sorbitol, compressible sugar and sucrose.

EXAMPLE 3—PREPARATION OF ORAL DOSAGE FORM

| Capsule Formula | |
|---|---|
| Ingredient | Percent by Weight |
| Zinc methotrexate | 0.001–50.0 |
| Lactose | 99.984–39.9 |
| Corn starch | 0.010–10.0 |
| Magnesium stearate | 0.005–0.1 |

The lactose, corn starch and magnesium stearate are added to a suitable blender and blended for 15–45 minutes or until blended uniformly. Zinc methotrexate is added and blended to uniformity. Suitable size hard gelatin capsules are then filled with this mixture with the aid of a capsule filling device. Alternate excipients for making these and other oral dosage forms include without limitation bentonite, calcium carbonate, magnesium oxide, magnesium carbonate, talc, silica gel, mannitol, tapioca powder and rice starch. Alternate glidants and lubricants for making these and other oral dosage forms include without limitation metallic stearates such as zinc stearate or calcium stearate; stearic acid; and glycol esters.

EXAMPLE 4—PREPARATION OF CREAMS FOR TOPICAL APPLICATION

| | Ingredient | Percent by Weight |
|---|---|---|
| Phase A: | Mineral oil | 4.0–7.0 |
| | Stearic acid | 1.0–4.0 |
| | Isopropyl palmitate | 0.5–1.0 |
| | Stearyl alcohol | 0.5–1.0 |
| | Cetyl alcohol | 1.5–2.5 |
| | Sorbitan stearate | 0.5–2.5 |
| | Polysorbate 60 | 0.5–1.0 |
| | Synthetic beeswax | 0.5–2.0 |
| | Preservative | 0.1–0.3 |
| Phase B: | Water | 83.3–37.4 |
| | Triethanolamine | 0.3–1.0 |
| | Glycerin | 2.0–5.0 |
| | Preservative | 0.1–0.3 |
| Phase C: | Zinc methotrexate | 0.1–10.0 |
| | Triethanolamine | 0.1–10.0 |
| | Water | 5.0–15.0 |

Phase (A) ingredients are heated to 75° C. and mixed well. This first mixture is maintained at 75° C. with continuous agitation The Phase (B) ingredients are mixed and stirred for 15 minutes at 70° C. This second mixture is maintained at 50° C. with stirring Phase (A) and Phase (B) are combined and stirred for 15 minutes at 70° C. The mixture is then maintained at 50° C. with stirring. Phase (C) is made by mixing zinc methotrexate and triethanolamine with stirring until the zinc methotrexate is dissolved and then adding water. Phase (C) is then added to the mixture of Phase (A) and Phase (B). The mixture is stirred until homogeneous then cooled to room temperature with continuous stirring.

EXAMPLE 5—PREPARATION OF LOTIONS FOR TOPICAL APPLICATION

| | Ingredient | Percent by Weight |
|---|---|---|
| Phase A: | Isopropyl myristate | 3.0–7.0 |
| | Cetyl alcohol | 0.4–0.8 |
| | Stearic acid | 0.6–0.9 |
| | Sorbitan laurate | 0.5–1.5 |
| | Polysorbate 60 | 1.5–3.0 |
| | Propylparaben | 0.1–0.3 |
| Phase B: | Water | 79.3–47.6 |
| | Triethanolamine | 0.3–0.6 |
| | Propylene glycol | 4.0–6.0 |
| | Methylparaben | 0.1–0.3 |
| Phase C: | Water | 0.1–10.0 |
| | Triethanolamine | 0.1–10.0 |
| | Zinc methotrexate | 0.1–10.0 |

The Phase (A) ingredients are heated to 70° C. and mixed well. The temperature of the mixture is maintained with continuous agitation. The Phase (B) ingredients are mixed and heated to 70° C. Phase (A) and Phase (B) are mixed and stirred for 15 minutes at 70° C. The mixture is then maintained at 50° C. with stirring. Phase (C) is formed by mixing zinc methotrexate and triethanolamine with stirring until zinc methotrexate is dissolved and adding water. Phase (C) is then added to the mixture of Phase (A) and Phase (B) and stirred until homogeneous. The mixture is then cooled to room temperature with continuous stirring.

EXAMPLE 6—PREPARATION OF SOLUTIONS FOR TOPICAL APPLICATION

| Ingredient | Percent by Weight |
|---|---|
| Zinc methotrexate | 0.1–10.0 |
| Triethanolamine | 0.1–10.0 |
| Propylene glycol | 1.0–5.0 |
| Preservatives | 0.1–0.3 |
| Water | 98.7–74.7 |

The zinc methotrexate and the triethanolamine are mixed in a suitable container and stirred until the zinc methotrexate is dissolved. Water is then added to the mixture with stirring. In a separate container, the preservatives are dissolved in propylene glycol. The propylene glycol-preservative mixture is then added to the zinc methotrexate solution and stirred.

From the foregoing it will be apparent to those skilled in the art that various modifications in the above-described compositions and methods can be made without departing from the scope and spirit of the invention. Accordingly, the invention may be embodied in other specific forms without departing from the spirit or essential characteristics thereof Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A composition comprising a pharmaceutically suitable carrier and a therapeutically effective amount of a compound of the general formula (I), (II), (III) or (IV):

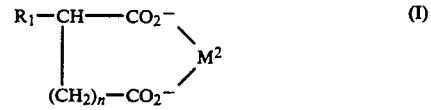

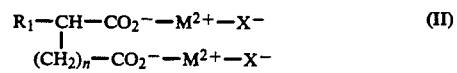

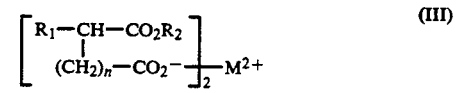

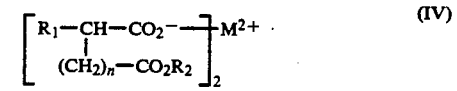

wherein n is 0 or an integer from 1 to 4, $M^{2+}$ is a divalent metal cation, $X^-$ is an anion, $R_2$ is hydrogen or an aliphatic, aromatic or arylalkyl group, and $R_1$ is of the general formula

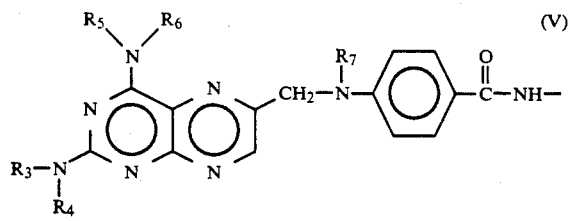

wherein $R_3$, $R_4$, $R_5$, $R_6$ and $R_7$ are hydrogen or an alkyl group of 1 to 5 carbons.

2. The composition of claim 1 wherein said divalent metal cation is selected from the group consisting of zinc, copper, cadmium and manganese.

3. The composition of claim 1 wherein $R_2$ is hydrogen, an alkyl, substituted alkyl, alkenyl or cycloalkyl group of 1 to 7 carbons, or a phenyl, benzyl or phenethyl group of 6 to 10 carbons, wherein the phenyl groups may be optionally substituted.

4. A composition comprising a pharmaceutically suitable carrier and a therapeutically effective amount of a compound of the general formula (I), (II), (III) or (IV):

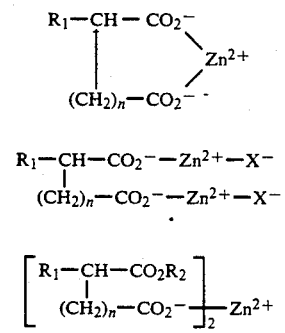

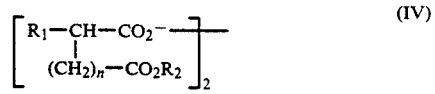

wherein n is 0 or an integer from 1 to 4, $X^-$ is an anion, $R_2$ is hydrogen or an aliphatic, aromatic or arylalkyl group, and $R_1$ is of the general formula (V):

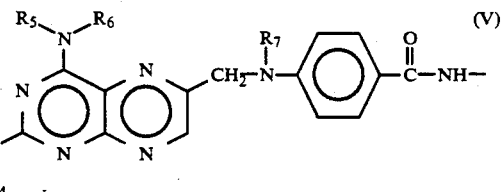

wherein $R_3$, $R_4$, $R_5$, $R_6$ and $R_7$ are hydrogen or an alkyl group of 1 to 5 carbons.

5. The composition of claim 4 wherein said zinc salt is of the general formula (III) or (IV).

6. The composition of claim 4 wherein $R_2$ is hydrogen, an alkyl, substituted alkyl, alkenyl or cycloalkyl group of 1 to 7 carbons, or a phenyl, benzyl or phenethyl group of 6 to 10 carbons, wherein the phenyl groups may be optionally substituted.

7. The composition of claim 4 wherein R2, R3, R4, R5 and R6 are hydrogen, R7 is methyl and n is 2.

8. The composition of claim 7 wherein said composition is an oral dosage form and said zinc salt constitutes 0.001 to 50.0 percent by weight of said composition.

9. The composition of claim 7 wherein said composition is a cream and said zinc salt constitutes 0.1 to 10.0 percent by weight of said composition.

10. The composition of claim 7 wherein said composition is a lotion and said zinc salt constitutes 0.1 to 10.0 percent by weight of said composition.

11. The composition of claim 7 wherein said composition is a solution and said zinc salt constitutes 0.1 to 10.0 percent by weight of said composition.

* * * * *

UNITED STATES PATENT AND TRADEMARK OFFICE
CERTIFICATE OF CORRECTION

PATENT NO.   : 5,166,149
DATED        : November 24, 1992
INVENTOR(S)  : Bernard Loev It is certified that error appears in the above-identified patent and that said Letters Patent is hereby corrected as shown below:

| Column | Line | |
|---|---|---|
| 7 | 28 | After "stirring" insert --.--. |
| 10 | 3 | Change "$\ldots \rbrack_2$" to --$\ldots \rbrack_2 Zn^{2+}$--. |

Signed and Sealed this

Second Day of November, 1993

Attest:

BRUCE LEHMAN

Attesting Officer   Commissioner of Patents and Trademarks